(12) United States Patent
Pishevar

(10) Patent No.: US 6,384,015 B1
(45) Date of Patent: May 7, 2002

(54) SELECTIVE LYSIS OF MALARIA INFECTED ERYTHROCYTES

(75) Inventor: Shervin K. Pishevar, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/831,993

(22) Filed: Apr. 1, 1997

(51) Int. Cl.⁷ .............................................. A61K 38/16
(52) U.S. Cl. ............................................ 514/12; 514/2
(58) Field of Search ........................................ 514/2, 12

(56) References Cited

PUBLICATIONS

Magowan et al. Blood, 86, 3196–3204, Oct. 1995.*
Gwadz, R. et al. Infection and Immunity, 57, 2628–2633, Sep. 1989.*
Matsuzaki et al., Biochemistry,34,6521–6526, 1995.*
Matsuzaki et al., Biochemistry,34,12553–12559, 1995.*
Matsuzaki et al., Biochemistry,34,3423–3429, 1995.*
Cabantchik et al. Blood Cells, 16, (2–3), 421–432, Feb. 1990.*
Pasvol, G. et al. Annals Tropical Medicine and Parasitology, 72, 87–88, Jan. 1978.*

* cited by examiner

Primary Examiner—Michael Borin
(74) Attorney, Agent, or Firm—Richard Aron Osman

(57) ABSTRACT

The invention provides methods and compositions for inhibiting the development of intracellular parasites by treating such cells with an effective concentration of a magainin, PGLa or XPF peptide under conditions whereby the development of the parasite in the cell is inhibited. The targeted parasites have been found to increase in the accessibility of the plasma membrane of said cell to the peptide, and particularly, to effect an increase in the cytopathic, especially lytic, sensitivity of the cell to the peptide. In one application, the invention provides methods for treating blood infected with a Plasmodium species, by contacting the blood with magainin 2 under conditions whereby the development of the Plasmodium in the infected erythrocytes is inhibited and the infected erythrocytes evidence relatively increased cytolytic sensitivity to the magainin.

18 Claims, 2 Drawing Sheets

SELECTIVE LYSIS OF MALARIA INFECTED ERYTHROCYTES

FIELD OF THE INVENTION

The field of the invention is the use of magainins and related peptides to selectively lyse malaria infected erythrocytes.

BACKGROUND OF THE INVENTION

Intracellular pathogens comprise a particularly intractable source of pathogenic infections. Notorious clinical examples include *Rickettsia, Chlamydia, Plasmodia* species. Malaria-causing *Plasmodia* species in particular are the most devastating sources of infectious human morbidity and mortality on earth, with approximately 250 million to 500 million new cases each year, malaria is the direct cause of 1 million to 1.5 million deaths per year. By seeking refuge inside host cells, intracellular pathogens such as Plasmodia are able to evade many traditional host defenses. Instead, the host must resort to immune mechanisms capable of distinguishing infected from uninfected cells.

Magainins, PGLa and XPF comprise a class of linear, amphipathic cationic peptides originally found in the skin of *Xenopus laevis* and shown to have broad-spectrum antimicrobial activity. These peptides have been reported to exhibit cidal activity against many infectious agents including bacteria, fungi, protozoa and viruses. In particular, magainins have been reported to disrupt extracellular stages of Plasmodia parasites. Unfortunately, the life cycles of the *Plasmodia*, like many intracellular pathogens, comprise only brief extracellular stages and the magainins were reported to have no effect on their intracellular development.

Relevant Literature

Gwadz et al. (1989) Infection and Immunity 57, 2628–2633 report that magainins had no effect on the intracellular development of *Plasmodium* species.

Zasloff (1989) U.S. Pat. No. 4,810,777 discloses a class of antibiotic polypeptides termed magainins.

Zasloff(1996) U.S. Pat. No. 5,567,681 discloses a antibiotic properties of polypeptides termed PGLa and XPF.

Huang et al. (1990) Antimicrobial Agents and Chemotherapy 34, 1824–1826 report the effect of magainins against pathogenic protozoa.

Aboudy et al. (1994) Int. J. Peptide Protein Res. 43, 573–582 report the effect of magainins against herpes simplex virus types 1 and 2.

Jacob and Zasloff (1994) Antimicrobial Peptides. While, Chichester (Ciba Foundation Symposium 186), p197–223 review the potential therapuetic applications of magainins.

Matsuzaki et al. (1995) Biochemistry 34, 3432–3429, report on the molecular basis for membrane selectivity of magainin 2.

Matsuzaki et al. (1994) Biochemistry 34, 3342–3349, report on the structural orientation of magainin 2 in phospholipid bilayers.

Tytler et al. (1995) Biochemistry 34, 4395–4401, report on the molecular basis for prokaryotic specificity of magainin-induced lysis.

SUMMARY OF THE INVENTION

The invention provides methods and compositions for inhibiting the development of intracellular parasites by treating such cells with an effective concentration of a magainin, PGLa or XPF peptide under conditions whereby the development of the parasite in said cell is inhibited. The targeted parasites have been found to increase in the accessibility of the plasma membrane of the cell to the peptide and effect an increase in the cytopathic, especially lytic, sensitivity of the cell to the peptide.

In one application, the invention provides methods for treating infected blood comprising both infected erythrocytes having an intracellular parasite and uninfected erythrocytes, by contacting the blood with a magainin, PGLa or XPF peptide under conditions whereby the development of the parasite in the infected erythrocytes is inhibited and the infected erythrocytes evidence relatively increased cytopathology relative to the uninfected cells.

In preferred embodiments of the disclosed methods, the infected cell is a resident erythrocyte, the parasite is a *Plasmodium* species, the peptide is magainin 2 and the conditions comprise a localized concentration of the peptide of between 5 and 100 $\mu$M.

DETAILED DESCRIPTION OF PARTICULAR EMBODIMENTS OF THE INVENTION

Figure 1:
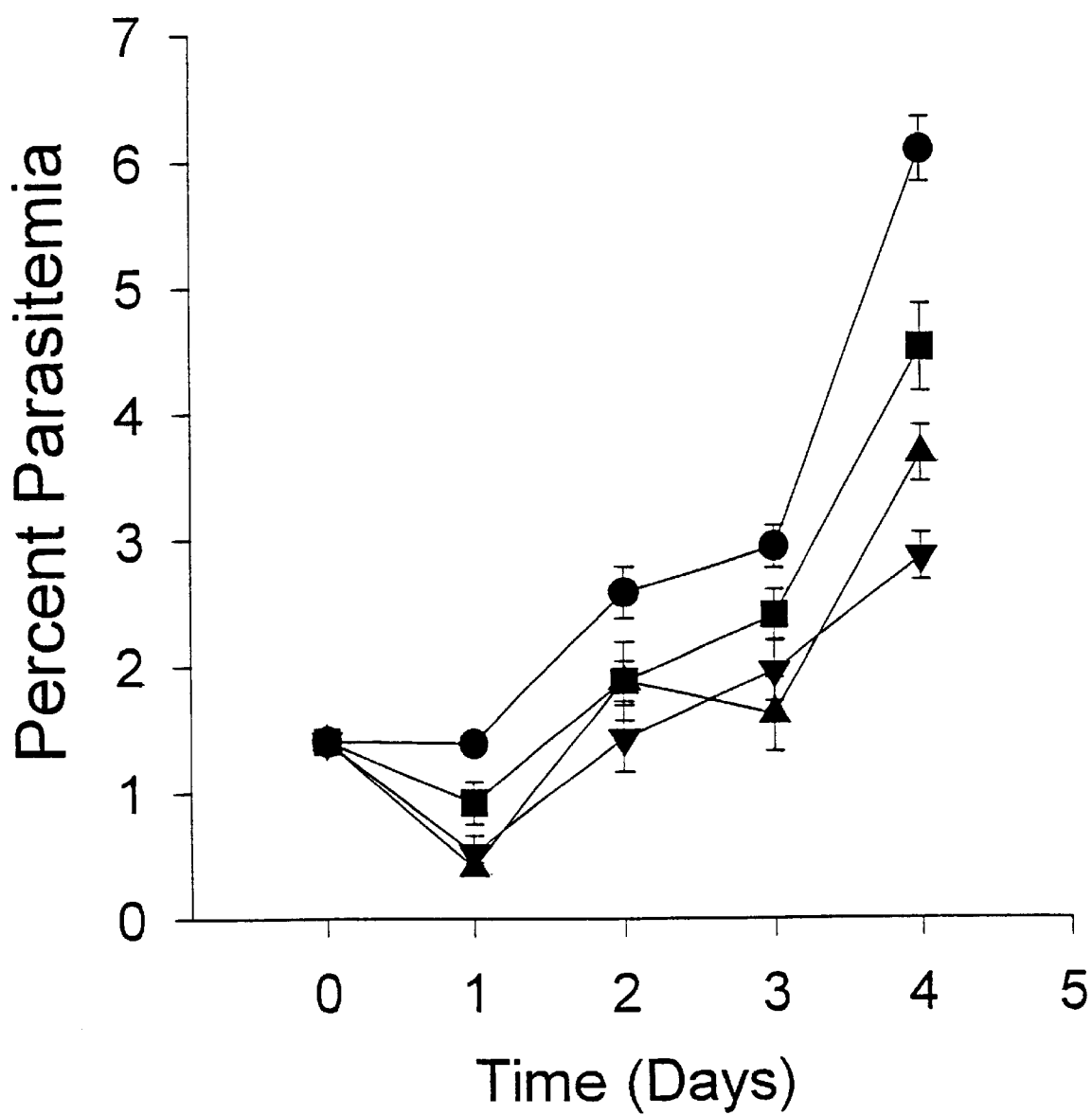
FIG. 1 shows the inhibition of parasitemia in *P. falciparum* infected human erythrocytes.

In one embodiment, the invention provides methods and compositions for inhibiting the development of intracellular parasites which cause an enhanced accessibility of the plasma membrane of the cell to a magainin, PGLa or XPF peptide, an enhanced sensitivity of the cell to peptide-induced cytopathology, or both. The enhanced accessibility may be assayed by peptide transfer into, across, or through the membrane, by, for example, immunofluorescent labeling. In a preferred embodiment, the enhanced accessibility results in an increase in plasma membrane permeability to the peptide of at least 50%, preferably at least 10-fold, preferably as measured by intracellular peptide, over uninfected cells. Enhanced sensitivity may be assayed by indicia of cytopathology such a changes in membrane potential (e.g. vital dye excludability), cellular dysfunction (e.g. structural deformations), etc.; especially, increased lytic sensitivity to one or more such peptides, over uninfected cells. Lytic sensitivity to the peptides may be measured by lysis as a function of peptide concentration, time, osmotic stress, etc.

Intracellular parasites which induce the requisite enhanced accessibility or sensitivity are readily determined empirically by screening in assays based on the requisite function, e.g. cell lysis assays. A wide variety of such intracellular parasites are amenable to screening, e.g. prokaryotes such as mycobacteria and *Rickettsia*, fungi such as *Chlamydia* and, especially, pathogenic protozoa such *Plasmodium* species, especially *P. vivax, P. malariae, P. ovale* and especially, *P. falciparum*.

In a preferred embodiment, the infected cells are blood cells, especially erythrocytes or red blood cells. The cells may be in culture or resident, i.e. in their native environment, for example, erythrocytes in the host, preferably mammalian host, blood stream. The route of administration to the cells depends on the nature and context of the cells. For example, the peptide may be solublized in a physiological buffer and added to culture media bathing cells in vitro or delivered to resident blood cells by direct injection into the animal host, ingestion by the host, etc., so long as the peptide achieves an effective localized concentration at the infected cell effective to inhibit development of a parasite therein.

In a particular embodiment, the peptide is administered in conjunction with an adjuvant or other antimicrobial therapeutic. For example, in the case of Plasmodia infections, the peptide may be administered in conjunction with a tissue schizonticide such as primaquine, or with a blood schizonticide such as chloroquine or for chloroquine-resistant Plasmodia, mefloquine, quinine, quinidine, pyrimethamine-sulfadoxine, doxycycline, halofantrine, artemisinin, etc.

Effective concentrations of the peptide are determined empirically, though a localized (e.g. proximal to the infected cell) concentrations between 1 and 500 μM, preferably between 5 and 100 μM, more preferably between 10 and 50 μM are shown to be effective in numerous applications, including *P. falciparum* infected blood-borne human erythrocytes. Inhibition may be measured by conventional assays for parasitemia, host physiology, etc.

The selection of a particular peptide for use in the subject method is determined by the targeted infected cell and parasite. As used herein, the magainin, PGLa and XPF peptides comprise a structurally related class of linear, amphipathic cationic peptides which may be naturally derived from epithelia of amphibians. Exemplary such peptides derivable from *Xenopus laevis* are known in the art (e.g. U.S. Pat. No. 4,810,777, supra, for exemplary magainins, and U.S. Pat. No. 5,567,681, supra, for exemplary PGLa and XPF peptides). Other magainin, PGLa and XPF peptides natural are readily identified by screening amphibian epithelia, preferably frog epithelia, more preferably *Xenopus laevis* epithelia, using extraction procedures and antimicrobial assays known in the art, e.g. Zasloff et al. (1987) Proc. Natl. Acad. Sci. USA 84, 5449–5453, or described herein. Such natural magainin, PGLa and XPF peptides are identical in sequence at at least 12, preferably at least 16, more preferably at least 20 positions of and/or share at least 8, preferably at least 12, more preferably at least 16 contiguous residues with a magainin, PGLa or XPF peptide as described in U.S. Pat. Nos. 4,810,777 or 5,567,681. For example, as described in Examples 1 and 2 below, *Xenopus laevis*-derived magainin 2 was found to be particular effective at selectively lysing *P. falciparum* infected blood-borne human erythrocytes as compared with non-infected cells.

The following examples are offered by way of illustration and not by way of limitation.

EXAMPLES OF THE INVENTION

Example 1

*P. falciparum* (New Guinean isolate D10) cultures were grown and maintained substantially as described in Trager et al. (1976) Science 193, 673–675. Human type O+ blood was obtained from healthy donors. Magainin 2 (Matsuzaki et al., 1995, supra) was made by solid phase peptide synthesis. Parasitemia assays were performed substantially as described in Pasvol et al (1978) Ann Trop Med Parasitol 72, 87–92 and Magowan et al. (1995) Blood 86, 3196–3204. The parasitemia assays were performed at 1, 24 and 48 hrs post-treatment at three magainin concentrations: 10, 25 and 50 uM final conc. magainin. Each group was done in triplicate and 7,500 erythrocytes were counted for each data point. Table 1 shows the resultant data. Table 1.

TABLE 1

| Magainin 2 | Day 1 | Day 2 | Day 3 | Day 4 |
|---|---|---|---|---|
| 0 uM | 1.39 | 2.59 | 2.96 | 6.09 |
| 10 uM | 0.92 | 1.88 | 2.40 | 4.52 |
| 25 uM | 0.41 | 1.88 | 1.61 | 3.68 |
| 50 uM | 0.52 | 1.43 | 1.96 | 2.87 |

FIG. 1 provides a graphical representation of the data showing the inhibition of parasitemia in infected human erythrocytes over the foregoing time courses and concentrations. In the figure, ● represents data points for the untreated cells, ■ represents data points for cells treated at 10 uM, ▲ at 25 uM, and ▼ at 50 uM. The data demonstrate dose and time dependent inhibitions of parasitemia by the magainin peptide.

Example 2

Figure 2:
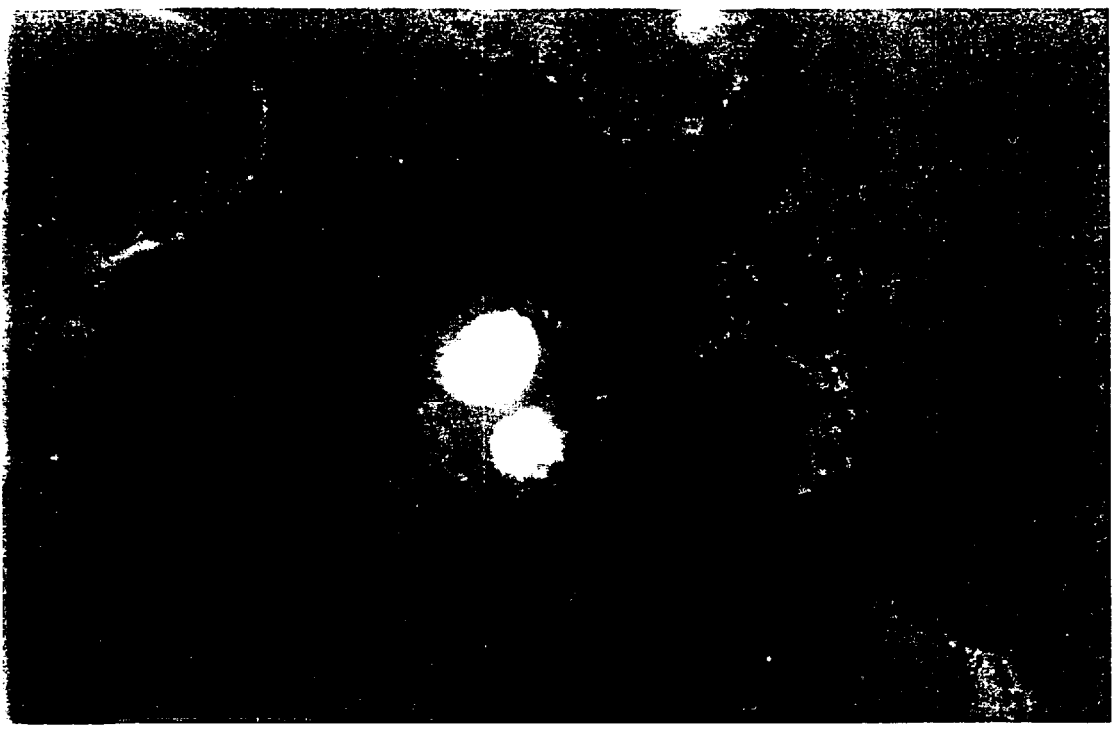
FIG. 2 shows an digitized image of a immunofluorescent micrograph of a *P. falciparum* infected human erythrocyte.

Immunofluorescent assays were carried out using a primary rabbit antibody generated against magainin 2 and a fluoresceine-goat anti-rabbit secondary antibody conjugate. The parasitemia assays were performed as described in Example 1 at 1, 24 and 48 hrs post-treatment at three magainin concentrations: 10, 25 and 50 uM final conc. magainin. Immunofluorescent. confocal microscopy was performed substantially as described in Magowan et al. (1995) Blood 86, 3196–3204. At each time point at each magainin concentration, the antibody was visualized exclusively within the parasite inside infected erythrocytes. No reaction was seen in any of the untreated or uninfected erythrocytes. FIG. 2 shows an immunofluorescent micrograph of an exemplary *P. falciparum* double-infected human erythrocyte after treatment with the magainin peptide at a 25 uM concentration.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for inhibiting the development of a parasite in a erythrocyte, said method comprising the step of contacting the erythrocyte, infected with an intracellular parasite, with a magainin, PGLa or XPF peptide under conditions whereby the development of said parasite in said erythrocyte is inhibited.

2. A method according to claim 1, wherein said parasite increases the accessibility of the plasma membrane of said cell to said magainin, PGLa or XPF peptide.

3. A method according to claim 1, wherein said parasite increases the lytic sensitivity of said cell to said magainin, PGLa or XPF peptide.

4. A method according to claim 1, wherein said cell is a human erythrocyte.

5. A method according to claim 1, wherein said magainin, PGLa or XPF peptide is magainin 2.

6. A method according to claim 1, wherein said parasite is a *Plasmodium* species.

7. A method according to claim 1, wherein said conditions comprise an effective concentration of said peptide of between 5 and 100 μM.

8. A method according to claim 1, wherein said parasite increases the lytic sensitivity of said cell to said magainin, PGLa or XPF peptide, said cell is a human erythrocyte, said parasite is a *Plasmodium* species, said magainin, PGLa or XPF peptide is magainin 2 and said conditions comprise an effective concentration of said magainin 2 of between 5 and 100 μM.

9. A method according to claim 8, wherein said cell is a resident human erythrocyte.

10. A method for inhibiting the intracellular development of a parasite said method comprising the step of contacting blood comprising both infected erythrocytes having an intracellular parasite and uninfected erythrocytes, with a magainin, PGLa or XPF peptide under conditions whereby the development of said parasite in said infected erythrocytes is inhibited and said infected erythrocytes evidence relatively increased cytopathology.

11. A method according to claim 10, wherein said parasite increases the accessibility of the plasma membrane of said cell to said magainin, PGLa or XPF peptide.

12. A method according to claim 10, wherein said parasite increases the lytic sensitivity of said cell to said magainin, PGLa or XPF peptide.

13. A method according to claim 10, wherein said cell is a human erythrocyte.

14. A method according to claim 10, wherein said magainin, PGLa or XPF peptide is magainin 2.

15. A method according to claim 10, wherein said parasite is a *Plasmodium* species.

16. A method according to claim 10, wherein said conditions comprise an effective concentration of said magainin, PGLa or XPF peptide of between 5 and 100 μM.

17. A method according to claim 10, wherein said parasite increases the lytic sensitivity of said cell to said magainin, PGLa or XPF peptide, said cell is a human erythrocyte, said parasite is a *Plasmodium* species, said magainin, PGLa or XPF peptide is magainin 2 and said conditions comprise an effective concentration of said magainin of between 5 and 100 μM.

18. A method according to claim 10, wherein said cell is a resident human erythrocyte.

* * * * *